US010028948B2

(12) United States Patent
Auclair et al.

(10) Patent No.: US 10,028,948 B2
(45) Date of Patent: Jul. 24, 2018

(54) CHROMONE DERIVATIVE AS A DOPAMINE D3 RECEPTOR ANTAGONIST FOR ITS USE FOR THE TREATMENT OF AUTISM SPECTRUM DISORDER

(71) Applicant: PIERRE FABRE MEDICAMENT, Boulogne-Billancourt (FR)

(72) Inventors: Agnès Auclair, Mazamet (FR); Paul Moser, Castres (FR); Pierre Sokoloff, Belleserre (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 53 days.

(21) Appl. No.: 15/103,470

(22) PCT Filed: Dec. 12, 2014

(86) PCT No.: PCT/EP2014/077635
§ 371 (c)(1),
(2) Date: Jun. 10, 2016

(87) PCT Pub. No.: WO2015/086836
PCT Pub. Date: Jun. 18, 2015

(65) Prior Publication Data
US 2016/0303117 A1    Oct. 20, 2016

(30) Foreign Application Priority Data
Dec. 13, 2013    (EP) ..................... 13306726

(51) Int. Cl.
*A61K 31/496* (2006.01)
*A61K 38/11* (2006.01)
*A61K 31/13* (2006.01)
*A61K 31/185* (2006.01)
*A61K 31/196* (2006.01)
*A61K 31/197* (2006.01)
*A61K 31/4168* (2006.01)
*A61K 31/55* (2006.01)
*A61K 45/06* (2006.01)

(52) U.S. Cl.
CPC ............ *A61K 31/496* (2013.01); *A61K 31/13* (2013.01); *A61K 31/185* (2013.01); *A61K 31/196* (2013.01); *A61K 31/197* (2013.01); *A61K 31/4168* (2013.01); *A61K 31/55* (2013.01); *A61K 38/11* (2013.01); *A61K 45/06* (2013.01)

(58) Field of Classification Search
CPC .................................................. A61K 31/496
See application file for complete search history.

(56) References Cited

U.S. PATENT DOCUMENTS 5,498,628 A    3/1996 Rognan et al.
2012/0157463 A1    6/2012 Sokoloff et al.

FOREIGN PATENT DOCUMENTS

| DE | 4229880 A1 | 3/1994 |
|---|---|---|
| EP | 0539281 A1 | 4/1993 |
| EP | 2263665 A1 | 12/2010 |
| FR | 2949465 A1 | 3/2011 |
| WO | WO 00/21951 A1 | 4/2000 |
| WO | WO 2006/034187 A2 | 3/2006 |
| WO | WO 2011/027289 A1 | 3/2011 |
| WO | WO 2011/150380 A1 | 12/2011 |
| WO | WO 2012/168411 A1 | 12/2012 |

OTHER PUBLICATIONS

Mayo Clinic. "Austism spectrum disorder." (c) 2017. Available from: < http://www.mayoclinic.org/diseases-conditions/autism-spectrum-disorder/diagnosis-treatment/treatment/txc-20337877?p=1 >.*
Hellings, J.A., et al. "Dopamine antagonists for treatment resistance in autism spectrum disorders: review and focus on BDNF stimulators loxapine and amitriptyline." Expert Op. Pharm. (2017), vol. 18, No. 6, pp. 581-588.*
Joyce, J., et al. "Dopamine D3 receptor antagonists as therapeutic agents." Drug Discovery Today. (Jul. 2005), pp. 917-925. Available from: < http://ac.els-cdn.com/S1359644605034914/1-s2.0-S1359644605034914-main.pdf?_tid=54798a2e-7a07-11e7-a7aa-00000aacb35e
&acdnat=1501955936_9c20f9a1becfcb1990528a2efd092c99 >.*
Abrahams et al., "Advances in autism genetics: on the threshold of a new neurobiology," Nature Reviews Genetics, vol. 9, No. 5, May 2008, pp. 341-355.
Bringas et al., "Rearrangement of the Dendritic Morphology in limbic Regions and Altered Exploratory Behavior in a Rat Model of Autism Spectrum Disorder," Neuroscience, vol. 241, 2013, pp. 170-187.
Bromley et al., "The prevalence of neurodevelopmental disorders in children prenatally exposed to antiepileptic drugs," Journal of Neurology, Neurosurgery & Psychiatry, vol. 84, 2013 (published online Jan. 31, 2013), pp. 637-643 (8 pages total).
Cussac et al., "[3H]S33084: a novel, selective and potent radioligand at cloned, human dopamine D3 receptors," Naunyn-Schmiedeberg's Archives of Pharmacology, vol. 361, 2000 (published online Mar. 17, 2000), pp. 569-572.
Cussac et al., "Human Dopamine D3 Receptors Mediate Mitogen-Activated Protein Kinase Activation Via a Phosphatidylinositol 3-Kinase and an Atypical Protein Kinase C-Dependent Mechanism," Molecular Pharmacology, vol. 56, 1999, pp. 1025-1030.
De Krom, "A Common Variant in DRD3 Receptor is Associated with Autism Spectrum Disorder," Biological Psychiatry, vol. 65, 2009, pp. 625-630.
Dendrinos et al., "Prenatal VPA exposure and changes in sensory processing by the superior colliculus," Frontiers in Integrative Neuroscience, vol. 5, Article 68, Oct. 20, 2011, pp. 1-12.
International Search Report (Form PCT/ISA/210), dated Jun. 2, 2015, for International Application No. International PCT/EP2014/077635.

(Continued)

*Primary Examiner* — Noble E Jarrell
*Assistant Examiner* — John S Kenyon
(74) *Attorney, Agent, or Firm* — Birch, Stewart, Kolasch & Birch, LLP

(57) ABSTRACT

The present invention claims a chromone derivative and pharmaceutical compositions and combinations comprising a least the said derivative, which is a dopamine D3 receptor antagonist, for their use for the treatment of autism spectrum disorder.

12 Claims, 1 Drawing Sheet

(56) References Cited

OTHER PUBLICATIONS

Jeanneteau et al., "A functional variant of the dopamine D3 receptor is associated with risk and age-at-onset of essential tremor," Proceedings of the National Academy of Sciences, vol. 103, No. 28, Jul. 11, 2006, pp. 10753-10758.

Kanner, "Autistic Disturbances of Affective Contact," Nervous Child, vol. 2, 1943, pp. 217-250.

Kataoka et al., "Autism-like behaviours with transient histone hyperacetylation in mice treated prenatally with valproic acid," International Journal of Neuropsychopharmacology, vol. 16, 2013 (published online Nov. 18, 2011), pp. 91-103.

King et al., "Double-blind, placebo-controlled study of amantadine hydrochloride in the treatment of children with autistic disorder," Database Medline, US National Library of Medicine, NLM11392343, XP-002720537, Jun. 2001, pp. 1-2.

Lannfelt et al., "Amino acid substitution in the dopamine D3 receptor as a useful polymorphism for investigating psychiatric disorders," Psychiatric Genetics, vol. 2, 1992, pp. 249-256.

Lemonnier et al., "A randomised controlled trial of bumetanide in the treatment of autism in children," Translational Psychiatry, vol. 2, 2012 (published online Dec. 11, 2012), pp. 1-8.

Markram et al., "Abnormal Fear Conditioning and Amygdala Processing in an Animal Model of Autism," Neuropsychopharmacology, vol. 33, 2008 (published online May 16, 2007), pp. 901-912 (21 pages total).

Martineau et al., "Catecholaminergic Metabolism and Autism," Developmental Medicine and Child Neurology, vol. 36, 1994, pp. 688-697.

Michalon et al., "Chronic Pharmacological mGlu5 Inhibition Corrects Fragile X in Adult Mice," Neuron, vol. 74, Apr. 12, 2012, pp. 49-56.

Persico et al., "Autism Genetics," Behavioural Brain Research, vol. 251, 2013 (available online Jun. 13, 2013), pp. 95-112.

Pritchard et al., "Linkage Disequilibrium in humans: Models and Data," The American Journal of Human Genetics, vol. 69, 2001 (electronically published Jun. 14, 2001), pp. 1-14.

Rapin et al., "Autism: Definition, Neurobiology, Screening, Diagnosis," Pediatric Clinics of North America, vol. 55, No. 5, 2008, pp. 1129-1146.

Roullet et al., "In utero exposure to valproic acid and autism—A current review of clinical and animal studies," Neurotoxicology and Teratology, vol. 36, 2013 (availbe online Feb. 8, 2013), pp. 47-56.

Schneider et al., "Behavioral Alterations in Rats Prenatally Exposed to Valproic Acid: Animal Model of Autism," Neuropsychopharmacology, vol. 30, 2005 (published online Jul. 7, 2004), pp. 80-89 (14 pages total).

Sokoloff et al., "Molecular cloning and characterization of a novel dopamine receptor (D3) as a target for neuroleptics," Nature, vol. 347, Sep. 13, 1990, pp. 146-151.

Staal et al., "Brief Report: The Dopamine-3-Receptor Gene (DRD3) is Associated with Specific Repetitive Behavior in Autism Spectrum Disorder (ASD)," The Journal of Autism and Developmental Disorders, vol. 42, 2012 (published online Jun. 21, 2011), pp. 885-888.

Tomson et al., "Teratogenic effects of antiepileptic drugs," The Lancet Neurology, vol. 11, Sep. 2012 (published online Jul. 16, 2012), pp. 803-813.

Won et al., "Autism spectrum disorder causes, mechanisms, and treatments: focus on neuronal synapses," Frontiers in Molecular Neuroscience, vol. 6, Article 19, Aug. 5, 2013, pp. 1-26.

Yochum et al., "Differential development of central dopaminergic and serotonergic systems in BALB/c and C57BL/6J mice," Brain Research, vol. 1349, 2010 (available online Jun. 17, 2010), pp. 97-104.

* cited by examiner

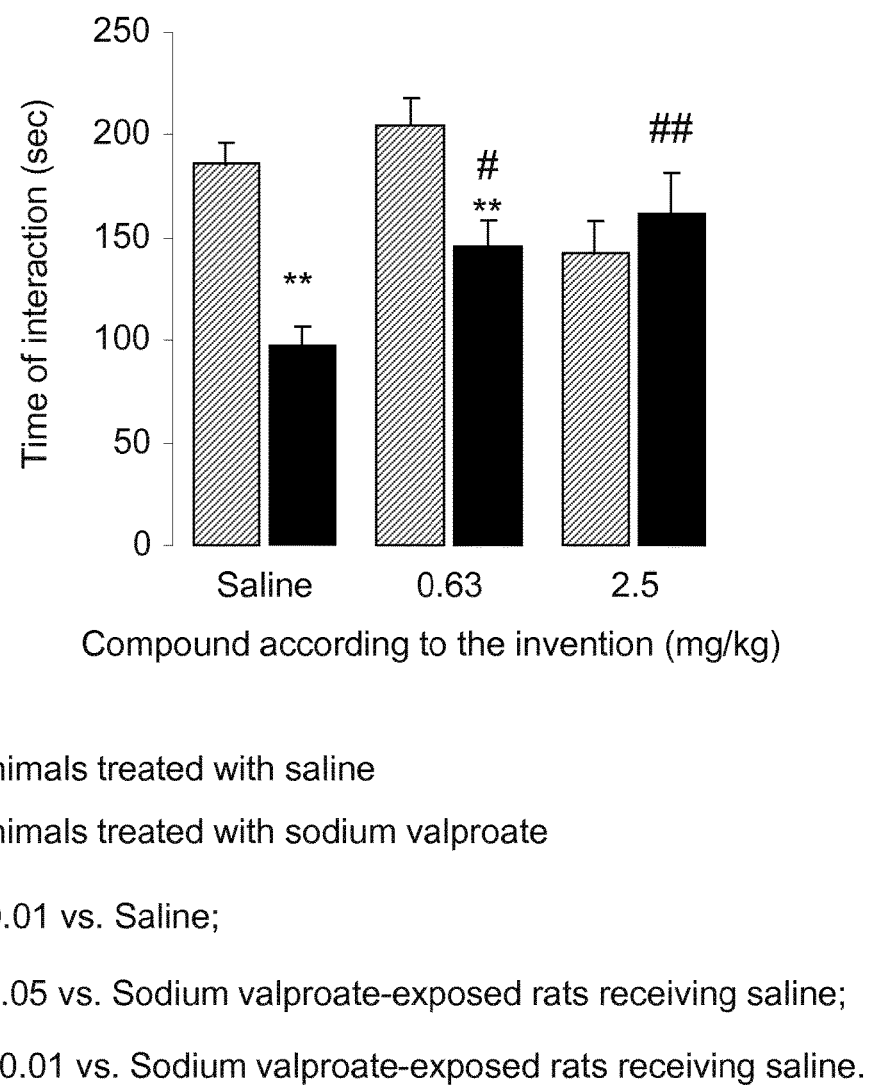
☒ Animals treated with saline
■ Animals treated with sodium valproate
** p<0.01 vs. Saline;
# p< 0.05 vs. Sodium valproate-exposed rats receiving saline;
## p< 0.01 vs. Sodium valproate-exposed rats receiving saline.

CHROMONE DERIVATIVE AS A DOPAMINE D3 RECEPTOR ANTAGONIST FOR ITS USE FOR THE TREATMENT OF AUTISM SPECTRUM DISORDER

The invention relates to the N-(3-{4-[4-(8-oxo-8H-[1,3]dioxolo[4,5-g]chromen-7-yl)-butyl]-piperazin-1-yl}-phenyl)-methanesulfonamide or a pharmaceutically acceptable salt thereof, for its use as medicament for the treatment of autism spectrum disorder.

Patent application WO 2011/027289 discloses chromone derivatives, a process for their preparation and their therapeutic applications for the treatment of neurological or psychiatric diseases. The chromone derivatives according to WO 2011/027289 are dopamine D3 receptor partial agonists or antagonists.

Notably, WO 2011/027289 discloses the N-(3-{4-[4-(8-Oxo-8H-[1,3]dioxolo[4,5-g]chromen-7-yl)-butyl]-piperazin-1-yl}-phenyl)-methanesulfonamide (Example N° 21 of WO 2011/027289) corresponding to formula 1.

Formula 1

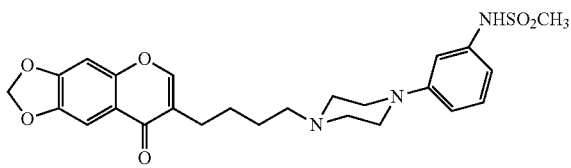

Among the diseases to be treated by the chromone derivatives, WO 2011/027289 claims Parkinson's disease, psychosis, schizophrenia, dyskinesias associated with Parkinson's disease, cognitive deficiency optionally associated with age or with Alzheimer's disease, mood disorder, essential tremor, anxiety, depression, bipolar disorder, sexual impotence, premature ejaculation, alcoholism and nicotine addiction. Notably, WO2011/027289 does not disclose nor claim neurodevelopmental disorders.

The neurodevelopmental disorders are a group of conditions with onset in the developmental period. These disorders typically manifest in childhood and are characterized by developmental deficits that produce impairment of personal, social, academic, or occupational functioning. The range of disabilities varies from very specific limitations of learning or control of executive functions to global impairments of social skills or intelligence.

Among neurodevelopmental disorders, autism has been characterized as an infantile trouble distinct from psychoses and its signs and symptoms described by Kanner in 1943 (L. Kanner "Autistic Disturbances of Affective Contact", Nervous Child 2:217-50, 1943), which includes various troubles in behaviour and skills. Autism included the typical infantile autism or Kanner's autism, Asperger's syndrome, which preserves language and cognitive functions and pervasive developmental disorder, not otherwise specified (commonly abbreviated as PDD-NOS), which was diagnosed when the full set of criteria for autism or Asperger syndrome were not met. Other classifications, like the International Statistical Classification of Diseases and Related Health Problems 10th Revision (ICD-10) from the World Health organization, includes even more subcategories. The variability of symptoms and presentations of autism among those various diagnostic categories made it difficult to comprehend to which particular symptom a therapeutic treatment was addressed.

Very recently however, the diagnosis of autism has markedly changed to recognize that social deficits distinguish autism and related disorders from other neurodevelopmental disorders (Rapin I, Tuchman R F. Autism: definition, neurobiology, screening, diagnosis. Pediatr Clin North Am. 2008; 55(5):1129-46) and to unify the diagnosis under the unique name of Autism Spectrum Disorder (ASD). According to the Diagnostic and Statistical Manual of Mental Disorders (DSM-5, American Psychiatric Association, *American Psychiatric Publishing*, Washington D.C., 2013), ASD is characterized by persistent deficits in social communication and social interaction across multiple contexts, including deficits in social reciprocity, non verbal communicative behaviors used for social interaction, and skills in developing, maintaining and understanding relationships. In addition to the social communication deficits, the diagnosis of autism spectrum disorder requires the presence of restricted, repetitive patterns of behaviors, interests, or activities.

Within the diagnosis of ASD, individual clinical characteristics are noted through the use of specifiers that describe the autistic symptoms and their severity. Thus, according to DSM-5, the disorder is diagnosed with the following diagnostic criteria:

A: Social Communication and Interaction across multiple contexts (all 3 required).
  deficits in social-emotional reciprocity.
  deficits in nonverbal communicative behaviors used for social interaction.
  deficits in developing and maintaining relationships.

B: Restricted, Repetitive Behavior (any 2 required).
  stereotyped or repetitive speech, motor movements, or use of objects.
  excessive adherence to routines, ritualized patterns of verbal or nonverbal behaviors, or excessive resistance to change.
  highly restricted, fixated interests that are abnormal in intensity of focus.
  hyper- or hypo-reactivity to sensory input or unusual interest in sensory aspect of environment.

C: Symptoms must be present in the early developmental period.

D: Symptoms cause clinically significant impairment of social, occupational, or other important areas of current functioning.

E: These disturbances are not better explained by intellectual disability or global developmental delay.

ASD is a highly inherited neuropsychiatric disorder: the concordance rate reaches up to 90% in monozygotic twins and 10% in dizygotic twins (reviewed in Won et al., *Front. Mol. Neurosci.* 2013, vol 6, art 19). However, ASD is an etiologically heterogeneous disorder in that no single genetic mutation accounts for more than 1-2% of cases (Abrahams et al., *Nat. Rev. Genet.* 2008, vol 9, p 341-355). Thus far, linkage and candidate-gene analyses, genome-wide association studies (GWAS), and assessments of chromosomal variations have uncovered a wide range of genes with predisposing mutations and polymorphisms associated with ASD (Persico et al., *Behav. Brain Res.* 2013, vol 251, p 95-112). None of these studies have identified the DRD3 as a susceptibility gene for ASD.

In 2009, de Krom and colleagues performed a genetic association study of 1,536 Single Nucleotide Polymorphisms (SNPs) present in 132 candidate genes in a sample of 144 patients with ASD and 404 control individuals (de Krom et al., *Biol. Psychiatr.*, 2009, vol 65, p 625-630). They found 31 single nucleotide polymorphisms positively associated at a P value lower than 0.01, which were tested in a second sample of 128 patients with ASD and 124 control individuals. Only the single nucleotide polymorphism rs167771 was found positively associated in the two ASD samples and in a joint statistical analysis. An association, which was not confirmed following statistical correction for multiple testing, was also found between the risk allele of rs167771 and a decreased risk of repetitive behaviour in patients with ASD, but not of other ASD symptomatic domains (Staal et al., *J. Autism Dev. Disord.* 2012, vol 42, p 885-888).

The single nucleotide polymorphism rs167771 is present in the second intron of the dopamine D3 receptor gene. The dopamine D3 receptor is almost exclusively expressed in the central nervous system, particularly in the ventral striatal area, a brain region that plays an important role in the control of emotions and cognition (Sokoloff et al., *Nature* 1990, vol 347, p 146-151). The dopamine D3 receptor exists in two allelic forms generated by a single nucleotide polymorphism named rs6280 (also known as CM033372 or BalI polymorphism) in the coding sequence, which leads to two amino acid sequences containing either a serine (Ser) or a glycine (Gly) residue at the $9^{th}$ position (Lannfelt et al., *Psychiatric Genetics* 1992, vol 2, p 249-256). The Gly/Gly allele is a gain-of-function allele, since it has a four times higher affinity for dopamine and is more responsive to dopamine than the Ser/Ser allele (Jeanneteau et al., *Proc. Natl. Acad. Sci. USA* 2006, vol 103, p 10753-10758). A therapeutic treatment based on intervention at the dopamine D3 receptor could be envisioned if the disorder to be treated is linked to either the gain-of-function (Gly/Gly allele) or loss-of-function (Ser/Ser allele). For instance, dopamine D3 receptor antagonists could be useful for treating a disorder linked to the Gly/Gly gain-of-function allele.

The e!Ensembl genetic database of the human genome (available at http://www.ensembl.org) indicates that the two single nucleotide polymorphisms rs167771 and rs6280 belong to the same contig NT_005612.16 of the assembly GRCh37.p10 and are separated by 14,540 base-pairs. Data from linkage disequilibrium tables (also available at http://www.ensembl.org), indicate partial linkage disequilibrium between rs167771 and rs6280, with r square values (Pritchard et al., *Am. J. Hum. Genet.*, 2001, vol 69, p 1-14) ranging from 0.245 to 0.610 in different populations. This indicates that the genetic association of rs167771 in ASD does not formally imply a linkage of ASD to the functional single nucleotide polymorphism rs6280 in dopamine D3 receptor. Accordingly, in another study on a small sample of 50 patients, rs6280 was not found to be associated with ASD (Martineau et al., *Dev Med Child Neurol*, 1994, 36:688-697).

There is no cure for ASD. Atypical antipsychotics, such as risperidone or aripiprazole, are approved by the US Food and Drugs Administration for the treatment of irritability associated with autistic disorder, including symptoms of aggression towards others, deliberate self-injury, temper tantrums and rapid mood changes, which do not belong to the core symptoms that define ASD. Adolescents and young adults with ASD are also prone to anxiety and depression, which can be treated with antidepressant drugs such as selective serotonin reuptake inhibitors. However, there is no approved treatment that targets the core symptoms ASD, i.e. deficits in social interactions and communication, and restricted interests.

Moreover, the genetic studies, are not conclusive and do not teach a method for treating ASD, especially the deficits in social interactions.

The inventors surprisingly found that the N-(3-{4-[4-(8-Oxo-8H-[1,3]dioxolo[4,5-g]chromen-7-yl)-butyl]-piperazin-1-yl}-phenyl)-methanesulfonamide disclosed in WO 2011/027289 was of great benefit in an animal model that recapitulates core symptoms of ASD, which is based on prenatal exposure to valproate.

FIG. 1 depicts the effects of acute administration of the compound of the invention on social interaction behavior of rats in the offspring of mothers treated with either saline or sodium valproate.

Valproic acid or its valproate salts, are anticonvulsant drugs, e.g. Depakote®, used to treat epilepsy, a common and diverse set of chronic neurological disorders characterized by unprovoked seizures. Valproate is also used in the treatment of bipolar disorder, a psychiatric mood disorder presenting with episodes of an elevated or agitated mood known as mania (or hypomania, depending on the severity) alternating with episodes of depression. Teratogenic effects (abnormalities linked to neural tube closure) of valproate have been known for 30 years from retrospective studies. Cases of ASD were also found in children from mothers who had taken valproate during their pregnancy, which led to warning on valproate and ASD risk in child-bearing women. Recently, the valproate-associated risk was confirmed by prospective studies, indicating that there is a 10-fold increase in the risk of ASD (Tomson et al., *Lancet Neurol.* 2012, vol 11, p 803-813; Bromley et al., *J. Neurol. Neurosurg. Psychiatry* 2013, vol 84, p 637-643). Valproate is supposed to cause ASD by interfering with epigenetic mechanism driving closure of the neural tube during intrauterine development (Kataoka et al., *Int. J. Neuropsychopharmacol.* 2013, vol 16, p 91-103).

In the ASD rat model, valproate is administered to pregnant females, at a determined embryonic day, typically the $12^{th}$ day, which corresponds to the time of neural tube closure in this species, and the offspring, when observed during infancy and adolescence, present with marked and specific behavioral abnormalities, accompanied by a few physical signs (reviewed in Roullet et al., *Neurotoxicol. Teratol.* 2013, vol 36, p 47-56). The valproate-induced behavioral abnormalities are strongly reminiscent of ASD symptoms and include:
  impairments of social behavior
  stereotyped/repetitive patterns of behavior
  sensory and communication impairment.
In addition, the phenotype also incorporates morphological rearrangements typical of ASD, such as reduced number or density of neuronal dendritic spines in the prefrontal cortex (Bringas et al., *Neuroscience* 2013, vol 241, p 170-187), which endows the valproate rat model with construct and face validities for a pathophysiological animal model of ASD.

In order to assess the potential of N-(3-{4-[4-(8-Oxo-8H-[1,3]dioxolo[4,5-g]chromen-7-yl)-butyl]-piperazin-1-yl}-phenyl)-methanesulfonamide hydrochloride, a potent dopamine D3 receptor antagonist (see Example 1) for treating ASD, the inventors have evaluated it in the ASD rat model (Example 2). As described in Example 2, the N-(3-{4-[4-(8-Oxo-8H-[1,3]dioxolo[4,5-g]chromen-7-yl)-butyl]-piperazin-1-yl}-phenyl)-methanesulfonamide hydrochloride was able to reverse social behavior deficit in prenatally valproate-exposed young rats administered as a single dose. The inventors thus showed that the said compound can be used to treat ASD.

As used above, the term "dopamine D3 receptor", "D3 receptor" or "DRD3" denotes a dopamine receptor sub-type chiefly expressed in the limbic system (Sokoloff P et al., Nature 1990, vol 347, p 146-151). Dopamine D3 receptor is described in international patent application WO 91/15513. As used above, the term "D3 receptor partial agonist" denotes a compound that forms a complex with dopamine D3 receptor and acts as a combined agonist-antagonist, that is to say it induces a physiological response of an intensity lower than that of the natural mediator, dopamine. In vitro, in a cell expressing dopamine D3 receptor, a dopamine D3 receptor partial agonist produces an active response the maximum intensity of which is lower than that produced by dopamine or by a full agonist, for example quinpirole (trans(−)-4aR-4,4a,5,6,7,8,8a,9-octahydro-5-propyl-1H(or 2H)pyrazolo[3,4g]quinoline). A dopamine D3 receptor partial agonist may also partially prevent the response produced by dopamine or other full agonists. As used above, the term "a dopamine D3 receptor antagonist" denotes a molecule that forms a complex with dopamine D3 receptor and is capable of preventing a response triggered by dopamine or an agonist thereof in a cell expressing dopamine D3 receptor.

As used here, the term "salts" denotes inorganic acid, organic acid, inorganic base or organic base addition salts of the compound of the present invention. As example, mention may be made of the salts derived from inorganic acids such as hydrochloric, hydrobromic, phosphoric, sulfuric acids, and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic acids. Preferably, the salts are pharmaceutically acceptable, that is to say, they are non-toxic for the patient to whom they are administered. The expression "pharmaceutically acceptable" refers to molecular entities and compositions that do not produce any adverse allergic effect or other undesirable reaction when administered to an animal or human. When used herein, the expression "pharmaceutically acceptable excipient" includes any diluent, adjuvant or excipient, such as preservative, filler disintegrator, wetting agent, emulsifier, dispersant, antibacterial or antifungal agent, or also agents that would allow intestinal and digestive absorption and resorption to be delayed. The use of those media or vectors is well known in the art. Except where the agent is chemically incompatible with the compound according to the invention, its use in pharmaceutical compositions containing the compound according to the invention is envisaged.

In the context of the invention, the term "treatment" as used herein means preventing or inhibiting the appearance or progression of the condition to which the term is applied, or of one or more symptoms of that condition. "Therapeutically active amount" means an amount of a the compound according to the invention that is effective in obtaining the desired therapeutic effect according to the invention. According to the invention, the term "patient" refers to a human affected or very susceptible to being affected by ASD.

According to the present invention, the compound (N-(3-{4-[4-(8-oxo-8H-[1,3]dioxolo[4,5-g]chromen-7-yl)-butyl]-piperazin-1-yl}-phenyl)-methanesulfonamide) or a pharmaceutically acceptable salt thereof, preferably hydrochloride, is used as a medicament for the treatment of ASD and notably the social interaction deficits.

The invention relates also to a treatment of ASD that comprises administering the compound (N-(3-{4-[4-(8-oxo-8H-[1,3]dioxolo[4,5-g]chromen-7-yl)-butyl]-piperazin-1-yl}-phenyl)-methanesulfonamide) or a pharmaceutically acceptable salt thereof in a therapeutically effective amount to a patient requiring treatment.

Moreover, the invention relates to pharmaceutical compositions containing the compound (N-(3-{4-[4-(8-oxo-8H-[1,3]dioxolo[4,5-g]chromen-7-yl)-butyl]-piperazin-1-yl}-phenyl)-methanesulfonamide) or a pharmaceutically acceptable salt thereof, and a pharmaceutically acceptable excipient, for their use as medicament for the treatment of ASD, notably the social interaction deficits.

As another embodiment, the invention relates to pharmaceutical compositions combining the compound (N-(3-{4-[4-(8-oxo-8H-[1,3]dioxolo[4,5-g]chromen-7-yl)-butyl]-piperazin-1-yl}-phenyl)-methanesulfonamide) or a pharmaceutically acceptable salt thereof, with other medications that are known to be used to treat ASD patients, and a pharmaceutically acceptable excipient, for their use as medicaments for the treatment of autism spectrum disorder, notably the social interaction deficits.

Preferably, the compound according to the invention is combined with a compound selected from the group consisting of memantine, amantadine, baclofen, R-baclofen, phenobam, acamprosate, bumetamide, carpipramine, oxytocin, vasopressin and mixtures thereof, and a pharmaceutically acceptable excipient.

The compositions according to the invention can be administered by the oral, transdermic, parenteral, nasal or rectal routes. The compositions can especially be administered by the oral route in an appropriate formulation. The dosages of the compound (N-(3-{4-[4-(8-oxo-8H-[1,3]dioxolo[4,5-g]chromen-7-yl)-butyl]-piperazin-1-yl}-phenyl)-methanesulfonamide) in the compositions of the invention can be adjusted to obtain an amount of active substance that is effective in obtaining the desired therapeutic response for a composition peculiar to the method of administration. The dosage level chosen depends therefore on the desired therapeutic effect, the administration route, the desired duration of treatment and other factors like patient body weight. The dosages can be from 0.001 to 10 mg per kg of body weight. The preferred dosages are in the range of 0.05 to 2 mg per kg of body weight.

The following examples illustrate the invention without limiting the scope thereof.

EXAMPLE 1

The N-(3-{4-[4-(8-oxo-8H-[1,3]dioxolo[4,5-g]chromen-7-yl)-butyl]-piperazin-1-yl}-phenyl)-methanesulfonamide hydrochloride was evaluated in vitro as a dopamine D3 receptor ligand and modulator of the activity of that receptor in accordance with the invention in cells expressing human recombinant dopamine D3 receptor or human recombinant dopamine D2 receptor. The inhibition constant (Ki) was measured by inhibition of the binding of [$^3$H] spiperone as described by Cussac et al., in *Naunyn-Schmiedeberg's Arch. Pharmacol.* 2000, vol 361, p 569-572. The inventors demonstrated that the compound according to the invention behaves as a potent dopamine D3 receptor ligand, with Ki values from 0.17 nanomole·liter$^{-1}$. This same compound exhibits a noticeable affinity for dopamine D2 receptor that is 71 times weaker.

Compound according to the invention was evaluated for its agonist, partial agonist, or antagonist activity at dopamine D3 receptor by using the MAP-kinase activity test on human recombinant dopamine D3 receptor (Cussac et al., *Mol. Pharmacol.* 1999, vol 56, p 1025-1030). The intrinsic activity of this compound was null, indicating that it is a full antagonist.

EXAMPLE 2

The N-(3-{4-[4-(8-oxo-8H-[1,3]dioxolo[4,5-g]chromen-7-yl)-butyl]-piperazin-1-yl}-phenyl)-methanesulfonamide hydrochloride was tested on social interaction of offspring of female rats which had been administered valproic acid as a sodium salt. The experimental settings of the valproic acid rat model of autism were adapted from published data (Dendrinos et al., *Front. Integr. Neurosci.* 2011, vol 5, art 68; Markram et al., *Neuropsychopharm.* 2007, vol 33, p 901-912; Schneider et al., *Neuropsychopharm.* 2005, vol 30, p 80-89).

Method:

Pregnant (embryonic day 8 max) female Sprague-Dawley rats [OFA (SD) Charles River Lyon, France] were quarantined for 4 days. Animals were group housed (2 per cage) in a full bottom cage (ML-H Cage, 370×235×180 mm, L×W× H; floor surface 870 $cm^2$) in an environmentally controlled room (temperature 21±1° C.; relative humidity 55±5%) under a 12-h light/dark cycle (lights on at 07:00 AM) with food (A04, Safe, Augy, France) and filtered water (0.2 μm pore diameter) freely available. Until weaning of offspring, animals were changed only once per week in order to disturb them as little as possible. Environmental enrichment (nesting material) was provided.

On embryonic days 12 and 13 (E12-E13), females were weighed and received three intraperitoneal injections of 2.4 ml/kg of sodium valproate (NaVPA, 200 mg/kg). Sodium valproate was dissolved in 0.9% saline for a concentration of 83.3 mg/ml, pH 7.3. Control dams received three intraperitoneal injections of saline (2.4 ml/kg). After the third injection, females were individually housed in ML-H type cages and allowed to raise their litters. Offspring were weaned between 21 to 23 days postnatally.

One sodium valproate- or saline-exposed rat and an unfamiliar naïve rat were placed in opposite corners of an arena (black arena 70 cm×70 cm×30 cm, L×I×H). Individual behavior related to social interaction such as following grooming, sniffing or biting the other rat as well as climbing over the other rat, initiated by the tested rat toward the unfamiliar rat were scored for a period of 10 min.

Results:

The effects of acute administration of the compound according to the invention on social interaction behavior in the offspring of mothers treated with either saline or sodium valproate are summarized on FIG. 1.

The data represented are the mean±the standard error of the mean for n=10 rats (5 females and 5 males).

The compound according to the invention had no significant effects on social interaction behavior in the offspring of saline-treated mothers.

At 0.63 mg/kg the compound according to the invention significantly reduced the social interaction deficits induced by prenatal exposure to sodium valproate. At 2.5 mg/kg the compound according to the invention completely reversed these deficits.

The compound according to the invention is considered as an interesting product to treat autism spectrum disorders and more particularly the deficit of social interactions.

The invention claimed is:

1. A method for inhibiting the appearance or progression of autism spectrum disorder or of one or more symptoms of autism spectrum disorder, comprising administering a compound N-(3-{4[4-(8-oxo-8H-[1,3]dioxolo[4,5-g]chromen-7-yl)-butyl]-piperazin-1-yl}-phenyl)-methanesulfonamide or a pharmaceutically acceptable salt thereof, in a therapeutically effective amount to a patient in need thereof.

2. The method of claim 1, wherein the pharmaceutically acceptable salt is hydrochloride.

3. The method of claim 1, for inhibiting the appearance or progression of social interaction deficits.

4. The method of claim 2, for inhibiting the appearance or progression of social interaction deficits.

5. A method for inhibiting the appearance or progression of autism spectrum disorder or of one ore more symptoms of autism spectrum disorder, comprising administering a pharmaceutical composition comprising N-(3-{4[4-(8-oxo-8H-[1,3]dioxolo[4,5-g]chromen-7-yl)-butyl]-piperazin-1-yl}-phenyl)-methanesulfonamide or a pharmaceutically acceptable salt thereof and a pharmaceutically acceptable excipient, in a therapeutically effective amount to a patient in need thereof.

6. The method of claim 5, wherein the pharmaceutically acceptable salt is hydrochloride.

7. The method of claim 5, for inhibiting the appearance or progression of social interaction deficits.

8. The method of claim 6, for inhibiting the appearance or progression of social interaction deficits.

9. The method of claim 5, wherein the pharmaceutical composition is combined with a compound selected from the group consisting of memantine, amantadine, baclofen, R-baclofen, phenobam, acamprosate, bumetamide, carpipramine, oxytocin, vasopressin and mixtures thereof.

10. The method of claim 6, wherein the pharmaceutical composition is combined with a compound selected from the group consisting of memantine, amantadine, baclofen, R-baclofen, phenobam, acamprosate, bumetamide, carpipramine, oxytocin, vasopressin and mixtures thereof.

11. The method of claim 7, wherein the pharmaceutical composition is combined with a compound selected from the group consisting of memantine, amantadine, baclofen, R-baclofen, phenobam, acamprosate, bumetamide, carpipramine, oxytocin, vasopressin and mixtures thereof.

12. The method of claim 8, wherein the pharmaceutical composition is combined with a compound selected from the group consisting of memantine, amantadine, baclofen, R-baclofen, phenobam, acamprosate, bumetamide, carpipramine, oxytocin, vasopressin and mixtures thereof.

* * * * *